United States Patent [19]

Remers

[11] Patent Number: 4,460,599
[45] Date of Patent: Jul. 17, 1984

[54] MITOMYCIN ANALOGS

[75] Inventor: William A. Remers, Tucson, Ariz.

[73] Assignee: University Patents, Inc., Norwalk, Conn.

[21] Appl. No.: 206,529

[22] Filed: Nov. 13, 1980

Related U.S. Application Data

[62] Division of Ser. No. 100,331, Dec. 5, 1979, Pat. No. 4,268,676.

[51] Int. Cl.³ .............................................. A61K 31/40
[52] U.S. Cl. .................................................... 424/274
[58] Field of Search .................... 424/274; 260/326.24

[56] References Cited

U.S. PATENT DOCUMENTS

| | | | |
|---|---|---|---|
| 3,332,944 | 7/1967 | Cosulich et al. | 424/274 |
| 3,410,867 | 11/1968 | Matsui et al. | 260/326.24 |
| 3,429,894 | 2/1969 | Matsui et al. | 260/326.24 |
| 3,450,705 | 6/1969 | Matsui et al. | 260/326.24 |
| 3,514,452 | 5/1970 | Matsui et al. | 424/274 |
| 4,231,936 | 11/1980 | Nakano et al. | 260/326.24 |
| 4,268,676 | 5/1981 | Remers | 424/274 |

*Primary Examiner*—Donald G. Daus
*Assistant Examiner*—William A. Teoli, Jr.
*Attorney, Agent, or Firm*—Marshall, O'Toole, Gerstein, Murray & Bicknell

[57] ABSTRACT

Compounds of the formula, I,

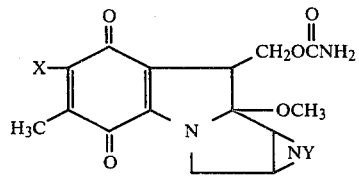

wherein: Y is hydrogen or lower alkyl; and X is a thiazolamino radical, a furfurylamino radical or a radical of the formula,

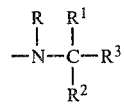

in which R, R¹, and R² are the same or different and selected from the group consisting of hydrogen and lower alkyl, and R³ is selected from the group consisting of lower alkenyl, halo-lower alkenyl, lower alkynyl, lower akloxycarbonyl, thienyl, formamyl, tetrahydrofuryl and benzene sulfonamide.

Also disclosed are novel methods for treatment of neoplastic disease states in animals, which methods comprise administering a therapeutically effective amount of a compound of the formula, Ia,

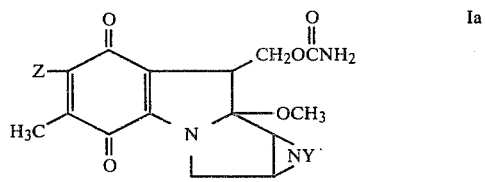

wherein: Y is hydrogen or lower alkyl; and Z is a thiazolamino radical, a furfurylamino radical, a cyclopropylamino radical, a pyridylamino radical, or a radical of the formula,

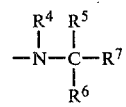

in which R⁴, R⁵, and R⁶ are the same or different and selected from the group consisting of hydrogen and lower alkyl, and R⁷ is selected from the group consisting of lower alkenyl, halo-lower alkenyl, lower alkynyl, lower alkoxycarbonyl, halo-lower alkyl, hydroxy-lower alkyl, pyridyl, thienyl, formamyl, tetrahydrofuryl, benzyl, and benzene sulfonamide.

4 Claims, No Drawings

MITOMYCIN ANALOGS

This is a division of application Ser. No. 100,331, filed Dec. 5, 1979, now U.S. Pat. No. 4,268,676.

BACKGROUND

The present invention relates generally to antibiotic mitosane compounds and to their use in the treatment of neoplastic disease states in animals.

Pertinent to the background of the invention are those antibiotics which are isolated from the fermented broth of *Streptomyces verticillatus* and named Mitomycin A, B, and C. The structures of these three compounds are well known in the art [being eludicated, for example, in a publication of J. S. Webb, et al., in J.A.C.S., 84, 3185(1962)] and are set out below.

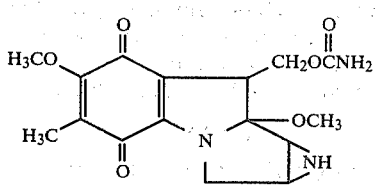

MITOMYCIN A

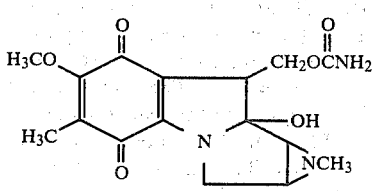

MITOMYCIN B

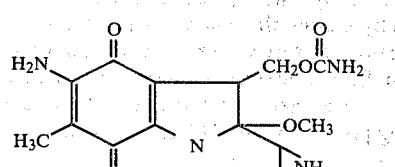

MITOMYCIN C

Mitomycin A, B, and C are acknowledged as excellent antibiotics but are relatively highly toxic to humans. This has prompted the prior art synthesis of numerous mitomycin derivatives and analogs in an attempt to secure compounds having equal or enhanced antibiotic activity but lesser toxicity than the naturally-occuring mitomycins. Among the mitomycin derivatives having structures and activities of interest to the present invention are those described in U.S. Pat. Nos. 3,332,944 (Colusich, et al.); 3,450,705 (Matsui, et al.); and 3,514,452 (Matsui, et al.), as well as in Kinoshita, et al., *J.Med.Chem.*, 14, No. 2, 103-112 (1971) and French Pat. No. 1,449,947.

Also of interest to the present invention are reports of workers in the art that certain mitomycins and mitomycin derivatives possess a degree of in vivo antitumor activity. See, e.g., Oboshi, et al., GANN, 58, 315-321 (1967); Usubuchi, et al., GANN, 58 307-313 (1967); Matsui, et al., *J. Antibiotics*, XXI, No. 3, 189-198 (1968); Japanese Pat. No. 68 06,627 to Matsui, et al. [as reported in Chem. Abstracts, Vol. 69, 86986K (1968)] and Cheng, et al., *J.Med.Chem.*, 20, No. 6, 767-770 (1977). The last-mentioned publication by the inventor and one of his co-workers discloses activity against P388 leukemia in mice for mitomycin A, mitomycin C and N-methylmitomycin A.

Mitomycin C is assertedly active against a relatively broad spectrum of experimental tumors including both hematological and solid types. In clinical practice, however, its use is limited to certain carcinomas owing to its toxicity and particularly its myelosuppressive effects. See, e.g., "Mitomycin C: Current Status and Development", Carter, et al. Eds., Academic Press, New York (1977). Numerous analogs of mitomycin C have been prepared in the hope of obtaining compounds with improved therapeutic properties, especially antitumor properties. The semi-synthetic analogs of the above-noted patents and publications have involved substituents on the aziridine ring, carbamoyl or acyl groups on the hydroxymethyl side chain, and replacement of the 7-substituent in the quinone ring with other functional groups, especially, substituted amines. None of these analogs has emerged as a clinical agent, although a 7-hydroxy analog of mitomycin C has received intensive study recently in Japan. This analog is asserted to be less leukopenic than mitomycin C, although it is also much less potent. Totally synthetic mitomycin analogs of the mitosene [Mott, et al., *J.Med.Chem.*, 21, 493 (1978)] and indoloquinone [Weiss, et al., *J.Med.Chem.*, 11, 742 (1968)] types have been prepared, but mainly for their antibacterial activity. The most active antitumor agent of the mitosene type is considerably less active than mitomycin C.

The art, therefore, persists in its search for new and useful compounds which are structurally related to the mitomycins, which possess antibiotic activity, have low toxicity and display a substantial degree of antitumor activity in animals.

SUMMARY

According to the present invention, there are provided novel compounds of the formula, I,

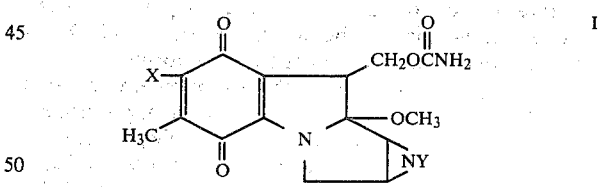

wherein: Y is hydrogen or lower alkyl; and X is a thiazolamino radical, a furfurylamino radical or a radical of the formula,

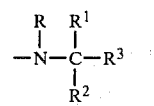

in which R, $R^1$, and $R^2$ are the same or different and selected from the group consisting of hydrogen and lower alkyl, and $R^3$ is selected from the group consisting of lower alkenyl, halo-lower alkenyl, lower alkynyl, lower akloxycarbonyl, thienyl, formamyl, tetrahydrofuryl and benzene sulfonamide.

Also provided according to the invention are novel methods for treatment of neoplastic disease states in animals, which methods comprise administering a therapeutically effective amount of a compound of the formula, Ia,

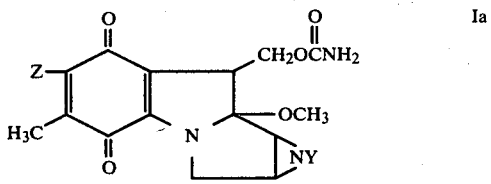

wherein: Y is hydrogen or lower alkyl; and Z is a thiazolamino radical, a furfurylamino radical, a cyclopropylamino radical, a pyridylamino radical, or a radical of the formula,

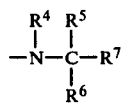

in which $R^4$, $R^5$, and $R^6$ are the same or different and selected from the group consisting of hydrogen and lower alkyl, and $R^7$ is selected from the group consisting of lower alkenyl, halo-lower alkenyl, lower alkynyl, lower alkoxycarbonyl, halo-lower alkyl, hydroxy-lower alkyl, pyridyl, thienyl, formamyl, tetrahydrofuryl, benzyl, and benzene sulfonamide.

The term "lower," as applied to "alkyl" radicals shall designate such straight or branched chain radicals as include from one to six carbon atoms. By way of illustration, "lower alkyl" shall mean and include methyl, ethyl, propyl, butyl, pentyl and hexyl radicals as well as ispropyl radicals, t-butyl radicals and the like. Similarly, "lower" as applied to "alkenyl" or "alkynyl" shall designate a radical having two to six carbon atoms.

It will be apparent that the compounds of formula I are all comprehended by the specifications of formula Ia. Put another way, all the novel antibiotic mitomycin derivatives of formula I are useful in practice of the novel antineoplastic therapeutic methods which involve administration of compounds of formula Ia.

Mitomycin derivatives of the invention are prepared by the reaction of mitomycin A with appropriately selected amine compounds. The N-alkylmitomycin (e.g., N-methylmitomycin) derivatives are similarly prepared by the reaction of a selected amine with N-alkylmitomycin A prepared from mitomycin C, e.g., according to the methods generally disclosed in Cheng, et al., *J.Med.Chem.*, 20, No. 6, 767–770 (1977). The preparative reactions generally yield the desired product as a crystalline solid which is readily soluble in alcohol.

Therapeutic methods of the invention comprehend the administration of effective amounts of one or more of the compounds of formula Ia, as an active ingredient, together with desired pharmaceutically acceptable diluents, adjuvants and carriers, to an animal suffering from a neoplastic disease state. Unit dosage forms of compounds administered according to the methods of the invention may range from about 0.001 to about 5.0 mg and preferably from about 0.004 to about 1.0 mg, of the compounds. Such unit dosage quantities may be given to provide a daily dosage of from about 0.1 to about 100 mg per kg, and preferably from about 0.2 to about 51.2 mg per kg, of body weight of the animal treated. Parental administration, and especially intraperitoneal administration, is the preferred route for practice of the inventive methods.

Other aspects and advantages of the present invention will become apparent upon consideration of the following description.

DESCRIPTION OF THE INVENTION

The following examples 1 through 25, describing preparation of certain presently preferred compounds according to the invention, are for illustrative purposes only and are not to be construed as limiting the invention. Unless otherwise indicated, all reactions were carried out at room temperature (20° C.), without added heat. Unless otherwise indicated, all thin layer chromatographic (TLC) procedures employed to check the progress of reactions involved the use of a pre-coated silica-gel plate and a mixture of acetone and benzene (4:1 by volume) as a developing solvent.

EXAMPLE 1

1,1a,2,8,8a,8b-Hexahydro-8-(hydroxymethyl)-8a-methoxy-5-methyl-6-(2-thiazolamino)-azirino[2',3':3,4-]pyrrolo-[1,2-a]indole-4,7-dione carbamate A mixture of potassium carbonate (80 mg) and 2-aminothiazole (18 mg) in 4 ml of anhydrous methanol was stirred under nitrogen atmosphere. To this mixture mitomycin A (30 mg or 0.085 mmol) was added with stirring. The progress of the reaction was checked periodically by TLC and the reaction appeared to be complete in 40 hours. The insoluble potassium carbonate was filtered and the filtrate was evaporated under reduced pressure. The residue obtained was chromatographed using silica-gel as adsorbent. The fraction obtained by eluting the column with a mixture of benzene and acetone (6:4 by volume) was evaporated. Recrystallization from a mixture of chloroform and acetone gave 16 mg (45% yield) of the desired product having a melting point of 85°–87° C. and providing the following analysis:

NMR (CDCl$_3$, TS): 'δ' values in ppm. The disappearance of a singlet at 4.02 (due to the 6-methoxy group in the starting materials) and the appearance of new signals at 6.46 (s,1), 7.36 (d,1) and 7.80 (d,1) were indicated.

EXAMPLE 2

1,1a,2,8,8a,8b-Hexahydro-8-(hydroxymethyl)-8a-methoxy-5-methyl-6-furfurylamino-azirino[2',3':3,4-]pyrrolo-[1,2-a]indole-4,7-dione carbamate To a solution of 60 mg (0.17 mmol) of mitomycin A in 8 ml of anhydrous methanol, 0.5 ml of furfurylamine was added with stirring. The progress of the reaction was periodically checked by TLC and the reaction appeared to be complete in 3 hours. The solvent was removed by evaporation under reduced pressure and the residue was chromatographed using silica-gel as adsorbent. The fraction obtained by eluting the column with ethyl acetate was evaporated. Recrystallization from a mixture of chloroform and here gave 30 mg (42.7% yield) of the desired product as colored crystals having a melting point of 62°–63° (decomposing) and providing the following analysis:

NMR (CDCl$_3$, TMS): 'δ' values in ppm. Absence of the 6-methoxy peak at 4.02, and the appearance of new peaks at 4.67(split s,2), 6.33–6.53(m,2) 6.57(t,1) and 7.33(split s,1) were indicated.

EXAMPLE 3

1,1a,2,8,8a,8b-Hexahydro-8-(hydroxymethyl)-8a-methoxy-1,5-dimethyl-6-furfurylamino-azirino[2′,3′:3,4-]pyrrolo-[1,2a]indole-4,7-dione carbamate To a solution of 50 mg (0.13 mmol) of N-methylmitomycin A in 6 ml of anhydrous methanol, 0.5 ml of furfurylamine was added with stirring. The solvent was removed by evaporation under reduced pressure and the residue was chromatographed using silica-gel as adsorbent. The fraction obtained by eluting the column with a mixture of chloroform and ethyl acetate (1:1 by volume) was evaporated under reduced pressure. Recrystallization from a mixture of chloroform and hexane gave 31 mg (55.7% yield) of the desired product as purple colored crystals having a melting point of 140°–141° (decomposing) and providing the following analyses:

NMR (CDCl$_3$, TMS): 'δ' values in ppm. Absence of the 6-methoxy peak at 4.02 ppm and the appearance of new peaks at 4.67(split s,2), 6.33–6.53(m,2), 6.57(t,1) and 7.33 (split s,1) were indicated.

EXAMPLE 4

1,1a,2,8,8a,8b-Hexahydro-8-(hydroxymethyl)-8a-methoxy-1,5-dimethyl-6-cyclopropylamino-azirino[2′,3′:3,4]pyrrolo-[1,2a]indole-4,7-dione carbamate To a solution of 75 mg (0.2 mmol) of N-methylmitomycin A in 10 ml of anhydrous methanol, 2 ml of cyclopropylamine was added with stirring. The reaction mixture was stirred overnight, whereupon TLC indicated no remaining starting material. The solvent was then evaporated under reduced pressure and the residue was chromatographed using silica-gel as adsorbent. The fraction obtained by eluting the column with ethyl acetate was evaporated under reduced pressure. Recrystallization from a mixture of methylene chloride and hexane gave 47.8 mg (59.7% yield) of the desired product as purple-colored crystals having a melting point of 166°–167° (decomposing) and providing the following analysis:

NMR (CDCl$_3$,TMS): 'δ' values in ppm. Absence of the 6-methoxy peak at 4.02 and the appearance of new peaks at 0.70–0.90(broad s,5) and at 6.30–6.43(broad s,1) was indicated.

EXAMPLE 5

1,1a,2,8,8a,8b-Hexahydro-8-(hydroxymethyl)-8a-methoxy-5-methyl-6-(3-pyridylamino)-azirino[2′,3′:3,4-]pyrrolo-[1,2-a]indole-4,7-dione carbamate To a solution of 60 mg mitomycin A (0.17 mmol) in 5 ml of anhydrous methanol was added 61 mg of 3-aminopyridine (1.2 mmol) with stirring. The progress of the reaction was checked periodically by TLC and the reaction appeared to be complete after 44 hours. The solvent was removed by evaporation under reduced pressure and the residue was chromatographed using silica-gel as adsorbent. The fraction obtained by eluting the column with a mixture of ethyl acetate and acetone (10:1 by volume) was evaporated to dryness. Recrystallization from chloroform gave 38 mg (56% yield) of green solid having a melting point of 78°–80° C. and providing the following analysis:

NMR (CDCl$_3$,TMS): 'δ' values in ppm. Absence of the 6-methoxy peak at 4.02 and the appearance of new peaks at 7.27 (s,2), 7.67(s,1) and 8.35 (s,2) were indicated.

EXAMPLE 6

1,1a,2,8,8a,8b-Hexahydro-8-(hydroxymethyl)-8a-methoxy-5-methyl-6-allylamino-azirino[2′,3′:3,4]pyrrolo-[1,2-a]indole-4,7-dione carbamate To a solution of 100 mg (0.28 mmol) of mitomycin A in 8 ml of anhydrous methanol, 150 mg (2.6 mmol) of allylamine was added with constant stirring. The reaction mixture was stirred overnight whereupon TLC indicated the absence of starting material. The solvent was then evaporated under reduced pressure and the residue was chromatographed using silica-gel as adsorbent. The fraction obtained by eluting the column from ethyl acetate was evaporated under reduced pressure. Recrystallization from a mixture of methylene chloride and hexane gave 29 mg (27.0% yield) of the desired product as purple-colored crystals having a melting point of 81°–82° (decomposing) and providing the following analysis:

NMR (CDCl$_3$,TMS): 'δ' values in ppm. Absence of the 6-methoxy peak at 4.02 and the appearance of peaks 3.30–3.43(m,2), 5.10(d,2), 5.50–6.10(m,1), 6.50(t,1) were indicated.

EXAMPLE 7

1,1a,2,8,8a,8b-Hexahydro-8-(hydroxymethyl)-8a-methoxy-1,5-dimethyl-6-allylamino-azirino[2′,3′:3,4-]pyrrolo-[1,2-a]indole-4,7-dione carbamate To a solution of 100 mg (0.275 mmol) of N-methylmitomycin A in 15 ml of anhydrous methanol, 58 mg (1 mmol) of allylamine was added with stirring. The reaction mixture was stirred overnight, whereupon TLC indicated the absence of starting material. The solvent was then evaporated under reduced pressure and the residue was chromatographed using silica-gel as adsorbent. The fraction obtained by eluting the colum with ethyl acetate was evaporated to dryness. Recrystallization from a mixture of ethyl acetate and hexane gave 38.5 mg (38% yield) of the desired product as purple-colored crystals having a melting point of 70°–71° C. (decomposing) and providing the following analysis:

NMR (CDCl$_3$,TMS): 'δ' values in ppm. Absence of the 6-methoxy peak at 4.02 and the appearance of peaks at 3.30–3.43(m,2), 5.10(d,2), 5.50–6.20(m,1), 6.50(t,1) were indicated.

EXAMPLE 8

1,1a,2,8,8a,8b-Hexahydro-8-(hydroxymethyl)-8a-methoxy-5-methyl-6-(2-methylallylamino)-azirino[2′,3′:3,4]pyrrolo-[1,2-a]indole-4,7-dione carbamate A solution of 50 mg mitomycin A (0.138 mmol) in 8 ml. of anhydrous methanol was stirred with 29 mg of 2-methylallylamine. The progress of the reaction was periodically checked by TLC and, after 2 hours, the solvent was removed by evaporation under reduced pressure and the residue was purified by column chromatography using silica-gel as adsorbent and ethyl acetate as the eluant. Recrystallization from a mixture of chloroform and hexane gave 30 mg (55% yield) of the desired product as purple crystals having a melting point of >250° C. (decomposing) and providing the following analysis:

NMR (CDCl$_3$,TMS) 'δ' values in ppm. Absence of the 6-methoxy peak at 4.02 and the appearance of new peaks at 1.97 (s,3), 4.00(d,2), 4.85 (d,2) and 6.53 (t,1) were indicated.

EXAMPLE 9

1,1a,2,8,8a,8b-Hexahydro-8-(hydroxymethyl)-8a-methoxy-1,5-dimethyl-6-(2-chloroallylamino)-azirino[2',3':3,4]pyrrolo-[1,2-a] indole-4,7-dione carbamate A solution of 50 mg (0.138 mmol) of N-methylmitomycin A in 6 ml of anhydrous methanol was stirred with 0.2 ml of 2-chloroallylamine. The progress of the reaction was checked periodically by TLC and appeared to be complete in 3 hours. The solvent was then evaporated under reduced pressure and the residue was chromatographed using silica-gel as adsorbent. The fraction obtained by eluting the column with a mixture of chloroform and ethyl acetate (1:1 by volume) was evaporated under reduced pressure. Recrystallization from a mixture of chloroform and hexane gave 20 mg (34% yield) of the desired product as purple-colored crystals having a melting point of 71°–72° C. (decomposing) and providing the following analysis:

NMR (CDCl$_3$,TMS): 'δ' values in ppm. Absence of the 6-methoxy peak at 4.02 and the appearance of new peaks at 4.03–4.55 (split s,2), 5.30–5.4 (broad s,2) and 6.53 (t,1).

EXAMPLE 10

1,1a,2,8,8a,8b-Hexahydro-8-(hydroxymethyl)-8a-methoxy-5-methyl-6-(N-methylpropargylamino)-azirino[2',3':3,4]pyrrolo[1,2-a]indole-4,7-dione carbamate To a solution of 50 mg (0.14 mmol) of mitomycin A in 10 ml of anhydrous methanol was stirred with 150 mg (2 mmol) of N-methylpropargylamine at room temperature. The reaction appeared to be completed in 3 hours, as revealed by TLC. The solvent was removed by evaporation under reduced pressure and the residue was chromatographed using silica-gel as adsorbent. The fraction obtained by eluting the column with ethyl acetate was evaporated under reduced pressure. Recrystallization from a mixture of methylene chloride and hexane gave 20 mg (37% yield) of the desired product as purple-colored crystals having a melting point of 86°–87° C. (decomposing) and providing the following analysis:

NMR (CDl$_3$, TMS): 'δ' values in ppm. Absence of the 6-methoxy peak at 4.02 and the appearance of new peaks at 2.00(s,1), 3.20 (s,3), 4.20(s,2) and 6.20–6.40(-broad s,1) were indicated.

EXAMPLE 11

1,1a,2,8,8a,8b-Hexahydro-8-(hydroxymethy)-8a-methoxy-5-methyl-6-(1,1-dimethylpropargylamino)-azirino[2',3':3,4]pyrrolo-[1,2-a]indole-4,7-dione carbamate To a solution of 50 mg (0.14 mmol) of mitomycin A in 6 ml of anhydrous methanol, 1 ml. of 1,1-dimethylpropargylamine was added with stirring. The progress of the reaction was checked by TLC and appeared to be complete after 72 hours. The solvent was then evaporated under reduced pressure and the residue was chromatographed using silica-gel as adsorbent. The fraction obtained by eluting the column with ethyl acetate was evaporated under reduced pressure. Recrystallization from a mixture of chloroform and hexane gave 11.6 mg (21% yield) of the desired product as purple-colored crystals having a melting point of 99°–100° C. (decomposing) and providing the following analysis:

NMR (CDCl$_3$,TMS): 'δ' values in ppm. Absence of the 6-methoxy peak at 4.02 and the appearance of new peaks at 1.68(s,6), 2.47(s,1) and 6.23–6.60(broad s,1) were indicated.

EXAMPLE 12

1,1a,2,8,8a,8b-Hexahydro-8-(hydroxymethyl)-8a-methoxy-5-methyl-6-propargylamino-azirino[2',3',:3,4-]pyrrolo-[1,2-a]indole-4,7-dione carbamate A solution of 100 mg (0.28 mmol) of mitomycin A in 10 ml of anhydrous methanol was stirred with 84 mg (1.5 mmol) of propargylamine for 4 hrs. The solvent was removed by evaporation under reduced pressure and the residue was chromatographed by using silica-gel as adsorbent. The fraction obtained by eluting the column with a mixture of ethyl acetate and acetone (8:2 by volume) was evaporated under reduced pressure. Recrystallization from a mixture of chloroform and hexane gave 36.5 mg (35% yield) of the desired product as purple-colored crystals having a melting point of 95°–96° (decomposing) and providing the following analysis:

NMR (CDCl$_3$,TMS): 'δ' values in ppm. Absence of the 6-methoxy peak at 4.02 and the appearance of peaks at 2.40(s,1), 4.33(s,2) and 6.37(t,1) were indicated.

EXAMPLE 13

1,1a,2,8,8a,8b-Hexahydro-8-(hydroxymethyl)-8a-methoxy-1,5-dimethyl-6-propargylamino-azirino[2',3':3,4]pyrrolo-[1,2-a]indole-4,7-dione carbamate A solution of 107 mg (0.27 mmol) of N-methylmitomycin A in 10 ml of anhydrous methanol was stirred with 85 mg (1.5 mmol) of propargylamine for 3 hours, whereupon TLC indicated no remaining starting material. The solvent was removed by evaporation under reduced pressure and the residue was chromatographed using silica-gel as adsorbent. The fraction obtained by eluting the column with ethyl acetate was evaporated under reduced pressure. Recrystallization from a mixture of methylene chloride and hexane gave 52.2 mg (50% yield) of the desired product as purple-colored crystals having a melting point of 86°–87° (decomposing) and providing the following analysis:

NMR (CDCl$_3$,TMS): 'δ' values in ppm. Absence of the 6-methoxy peak at 4.02 and the appearance of new peaks at 2.40(s,1), 4.33(s,2), and 6.38(t,1) were indicated.

EXAMPLE 14

1,1a,2,8,8a,8b-Hexahydro-8-(hydroxymethyl)-8a-methoxy-5-methyl-6-(methoxycarbonyl-methylamino)-azirino[2',3':3,4]pyrrolo-[1,2-a]indole-4,7-dione carbamate A solution of 40 mg of the methyl ester of glycine hydrochloride (0.42 mmol) in anhydrous methanol was cooled in ice-bath. To this cold solution a methanolic solution of 23 mg sodium methoxide (0.42 mmol) was added with stirring. A solution 76 mg of mitomycin A (0.21 mmol) in 45 ml of anhydrous methanol was added to this mixture with stirring under a nitrogen atmosphere. The resultant mixture was stirred at room temperature and the progress of the reaction was checked by TLC. The reaction appeared to be complete in 3.5 hours. Solvent was removed by evaporation under reduced pressure and the residue was purified by preparative thin-layer chromatograph to give 6 mg (13% yield) of the desired product having a melting point of 95°–97° and providing the following analysis:

NMR (CDCl$_3$,TMS): 'δ' values in ppm. Absence of the 6-methoxy peak at 4.02 and the appearance of new peaks at 3.50 (s,2), 3.73 (s,3) and 5.33–5.66 (broad s,1) were indicated.

EXAMPLE 15

1,1a,2,8,8a,8b-Hexahydro-8(hydroxymethyl)-8a-methoxy-1,5-dimethyl-6-(2-chloroethylamino)-azirino[2',3':3,4]pyrrolo-[1,2-a]indole-4,7-dione carbamate To a solution of 33 mg (0.09 mmol) of N-methylmitomycin A in 5 ml of anhydrous methanol, a solution of 56 mg of 2-chloroethylamine hydrochloride (0.5 mmol) in 2.5 ml of methanol and a solution of 41 mg sodium acetate (0.5 mmol) in 2.5 ml of methanol were added alternatively with constant stirring over a period of 10 minutes. The stirred reaction mixture was checked frequently by TLC and the reaction appeared to be complete in 24 hours. The solvent was evaporated and the residue was chromatographed using silica-gel as adsorbent. The fraction obtained by eluting the column with ethyl acetate was evaporated under reduced pressure. Recrystallization from a mixture of chloroform and hexane gave 16 mg (38% yield) of the desired product as purple-colored crystals having a melting point of 73°–74° C. (decomposing) and providing the following analysis: NMR (CDCl$_3$,TMS): 'δ' values in ppm. Absence of the 6-methoxy peak at 4.02 and the appearance of new peaks at 3.30–4.00(2t,4), 6.57(t,1) were indicated.

EXAMPLE 16

1,1a,2,8,8a,8b-Hexahydro-8-(hydroxymethyl)-8a-methoxy-5-methyl-6-(2-chloroethylamino)-azirino[2',3':3,4]pyrrolo-[1,2-a]indole-4,7-dione carbamate.

To a solution of 100 mg mitomycin A (0.286 mmol) in 10 ml. of anhydrous methanol, a solution of 82 mg sodium acetate (1 mmol) in 2.5 ml. of methanol and a solution of 116 mg 2-chloroethylamine hydrochloride (1 mmol) in 2.5 ml. of methanol were added alternatively with constant stirring, over a period of ten minutes. The stirred reaction mixture was periodically checked by TLC and the reaction appeared to be complete in 24 hours. The insoluble sodium chloride was removed by filtration and the solvent was removed by evaporation under reduced pressure. The residue was purified by column chromatography using ethyl acetate and acetone (4:1 by volume) as the eluant. Recrystallization from a mixture of chloroform and hexane gave 34 mg. (30% yield) of the desired product as purple-colored crystals having a melting point of 59° C. (decomposing) and providing the following analysis:

NMR (CDCl$_3$,TMS): 'δ' values in ppm. Absence of the 6-methoxy peak at 4.02 and the appearance of new peaks at 3.30–4.00 (m,4) and 6.40(t,1) were indicated.

EXAMPLE 17

1,1a,2,8,8a,8b-Hexahydro-8-(hydroxymethyl)-8a-methoxy-5-methyl-6-(3-chloropropylamino)-azirino[2',3':3:4]pyrrolo-[1,2-a]indole-4,7-dione carbamate.

To a solution of 100 mg mitomycin A (0.286 mmol) in 10 ml of anhydrous methanol, a solution of 82 mg sodium acetate (1 mmol) in 2.5 ml. of methanol and a solution of 130 mg 3-chloropropylamine hydrochloride (1 mmol) in 2.5 ml. of methanol were added alternatively with constant stirring over a period of ten minutes. The stirred reaction mixture was periodically checked by TLC and the reaction appeared to be complete in 24 hours. The insoluble sodium chloride precipitate was removed by filtration and the solvent was removed by evaporation under reduced pressure. The residue was purified by column chromatography using silica-gel as adsorbent and a mixture of ethyl acetate and acetone (4:1 by volume) as the eluant. Recrystallization from a mixture of chloroform and hexane gave 35 mg. (30% yield) of the desired product as colored crystals having a melting point of 64° C.(decomposing) and providing the following analysis:

NMR (CDCl$_3$,TMS), 'δ' values in ppm. Absence of the 6-methoxy peak at 4.02 and the appearance of new peaks at 1.87–2.30 (m,2) 3.55–3.95 (m,4), and 6.28 (t,1) were indicated.

EXAMPLE 18

1,1a,2,8,8a,8b-Hexahydro-8-(hydroxymethyl)-8a-methoxy-1,5-dimethyl-6-(3-hydroxypropylamino)-azirino[2',3':3,4]pyrrolo-[1,2-a]indole-4,7-dione carbamate (7)

To a solution of 50 mg(0.13 mmol) of N-methylmitomycin A in 10 ml of anhydrus methanol, a solution of 82 mg (1 mmol) sodium acetate in 2.5 ml of methanol and a solution of 130 mg (1 mmol) of 3-hydroxypropylamine hydrochloride in 2.5 ml of methanol were added alternatively with vigorous stirring, over a period of 10 minutes. The progress of the stirred reaction was checked frequently by TLC and appeared to be complete in 24 hours. The solvent was evaporated under reduced pressure and the residue was chromatographed using silica-gel as adsorbent. The fraction obtained by eluting the column with ethyl acetate was evaporated. Recrystallization from a mixture of methylene chloride and hexane gave 31 mg. (61% yield) of the desired product as purple-colored crystals having a melting point of 139°–140° (decomposing) and providing the following analysis:

NMR (CDCl$_3$,TMS): 'δ' values in ppm. Absence of the 6-methoxy pead at 4.02 and the appearance of new peaks at 1.80–2.13(m,2), 3,43–4.00(m,4), and 6.34(t,1) were indicated.

EXAMPLE 19

1,1a,2,8,8a,8b-Hexahydro-8-(hydroxymethyl)-8a-methoxy-5-methyl-6-(3-hydroxypropylamino)-azirino[2',3':3,4]pyrrolo-[1,2-a]indole-4,7-dione carbamate To a solution of 60 mg mitomycin A (0.17 mmol) in 5 ml of anhydrous methanol was added with stirring 0.5 ml of 3-hydroxypropylamine. The progress of the reaction was checked by TLC and the reaction appeared to be complete in two hours. The solvent was removed by evaporation under reduced pressure. The residue was dissolved in 100 ml of ethyl acetate and the organic layer was washed with water, dried over anhydrous sodium sulfate, and the solvent was removed by evaporating under reduced pressure. The residue was then chromatographed using silica-gel as adsorbent. The fraction obtained by eluting the column with a mixture of ethyl acetate and acetone (9:1 by volume) was evaporated to dryness under reduced pressure. Recrystallization from acetone gave 60.7 mg (91% yield) of the desired product as purple crystals having a melting point of >250° (decomposing and providing the following analysis:

NMR (CDCl$_3$,TMS): 'δ' values in ppm. Absence of the 6-methoxy peak at 4.02 and the appearance of new peaks at 1.52–1.92 (m,2), 3.43–4.00 (m,4), and 6.73(t,1) were indicated.

EXAMPLE 20

1,1a,2,8,8a,8b-Hexahydro-8-(hydroxymethyl)-8a-methoxy-5-methyl-6-(3-pyridylmethylamino)-azirino[2′,3′:3,4]pyrrolo-[1,2-a]indole-4,7-dione carbamate To a solution of 115 mg mitomycin A (0.33 mmol) in 5 ml of anhydrous methanol, 71 mg 3-aminomethylpyridine (0.66 mmol) was added and the mixture was stirred. The progress of the reaction was checked by TLC and appeared to be complete in 16 hours. The solvent was removed by evaporation under reduced pressure. The residue was chromatographed using silica-gel as adsorbent. The fraction obtained by eluting the column with a mixture of chloroform and ethyl acetate (1:1 by volume) was evaporated to give 107 mg (76% yield) of the desired product as purple-colored crystals having a melting point of 116°–118° after recrystallization from chloroform-hexane and providing the following analysis:

NMR (CDCl$_3$,TMS): 'δ' values in ppm. Absence of a 6-methoxy peak at 4.02 and the appearance of new peaks at 3.88 (s,2), 6.58 (t,1), 7.00–7.40 (d,1), 7.43–7.90 (d,1) and 8.53(s,2) were indicated.

EXAMPLE 21

1,1a,2,8,8a,8b-Hexahydro-8-(hydroxymethyl)-8a-methoxy-5-methyl-6-(2-thienylmethylamino)-azirino[2′,3′:3,4]pyrrolo-[1,2-a]indole-4,7-dione carbamate To a solution of 25 mg mitomycin A (0.071mmol) in 2 ml. of anyhdrous methanol, 16.2 mg 2-aminomethylthiophene (0.143 mmol) was added with stirring. The progress of the reaction was checked periodically by TLC and the reaction appeared to be complete in 24 hours. Removal of the solvent by evaporation under reduced pressure gave a dark-blue residue. The residue was purified by preparative thin-layer chromatography using a pre-coated silica-gel plate (2 mm thickness) and acetone as developing solvent. The product was further purified by recrystallizing from a mixture of chloroform and hexane to give 20 mg (65% yield) of the desired product having a melting point of 92°–94° C. and providing the following analysis:

NMR (CDCl$_3$,TMS): 'δ' values in ppm. Absence of the 6-methoxy peak at 4.02 and the appearance of new peaks at 3.72 (s,2), 6.47 (t,1) and 6.77–7.33 (m,3) were indicated.

EXAMPLE 22

1,1a,2,8,8a,8b-Hexahydro-8-(hydroxymethyl)-8a-methoxy-5-methyl-6-(aminocarbonylmethylamino)-azirino[2′,3′:3,4]pyrrolo-[1,2-a]indole-4,7-dione carbamate A mixture of mitomycin A (40 mg, 0.11 mmol) and glycinamide (42 mg) in 3.5 ml of absolute ethanol was stirred at room temperature for 4 hours. The solvent was evaporated under reduced pressure and the residue was purified by preparative thin-layer chromatography using a pre-coated silica-gel plate (2 mm thickness) and a mixture of ethanol and ethyl acetate (1:3 by volume) as developing solvent. The blue zone was eluted with ethanol and evaporated under reduced pressure to give 12.8 mg (29.7% yield) of the desired product having a melting point of 124°–126° C. and providing the following analysis:

NMR (CDCl$_3$,TMS): 'δ' values in ppm. Absence of the 6-methoxy peak at 4.02 and the appearance of new peaks at 3.95 (s,2), 5.36 (broad, 2) and 6.35 (m,1) were indicated.

EXAMPLE 23

1,1a,2,8,8a,8b-Hexahydro-8-(hydroxymethyl)-8a-methoxy-5-methyl-6-(2-tetrahydrofurfurylamino)-azirino[2′,3′:3,4]pyrrolo-[1,2-a]indole-4,7-dione carbamate To a solution of 100 mg mitomycin A (0.3 mmol) in 8 ml of anhydrous methanol, 0.2 ml of tetrahydrofurfurylamine was added with stirring. The progress of the reaction was checked by TLC using a pre-coated silica-gel plate and acetone as developing solvent. The reaction appeared to be complete in 3 hours. The solvent was removed by evaporation under reduced pressure and the residue was chromatographed using silica-gel as adsorbent. The fraction obtained by eluting the column with ethyl acetate was evaporated under reduced pressure. Recrystallization from a mixture of chloroform and pentane gave 52 mg (43.5% yield) of the desired product as a dark-blue solid having a melting point of 236°–237° C. (decomposing) and providing the following analysis:

NMR (CDCl$_3$,TMS): 'δ' values in ppm. Absence of the 6-methoxy peak at 4.02 and the appearance of new signals at 1.26 (s,2), 1.66–2.37 (m,4), 3.50–4.10 (m,3) and 6.55 (t,1) were indicated.

EXAMPLE 24

1,1a,2,8,8a,8b-Hexahydro-8-(hydroxymethyl)-8a-methoxy-5-methyl-6-phenylethylamino-azirino[2′,3′:3,4]pyrrolo-[1,2-a]indole-4,7-dione carbamate To a solution of 115 mg of mitomycin A (0.33 mmol) in 4 ml of anydrous methanol was added with stirring 80 mg of phenylethylamine (0.66 mmol) in 2 ml of anhydrous methanol. After 18 hours, the solvent was removed by evaporation under reduced pressure. The residue was dissolved in 15 ml of ethyl acetate, and then washed with five 15 ml portions of pH 4 buffer solution. The solvent was removed under reduced pressure and the residue was chromatographed using silica gel as adsorbent and ethyl acetate as solvent. Recrystallization of the product from ethyl acetate-ether gave 85 mg (58.7% yield) of purple solid having a melting point of 94°–96° C. and providing the following analysis:

NMR (CDCl$_3$,TMS): 'δ' values in ppm. Absence of the 6-methoxy peak at 4.02 and the appearance of new peaks at 3.40–3.90 (m,4), 6.33(t,1) and 7.27 (s,5) were indicated.

EXAMPLE 25

1,1a,2,8,8a,8b-Hexahydro-8-(hydroxymethyl)-8a-methoxy-5-methyl-6-[(4-sulphonamidophenyl)methylamino]-azirino[2',3':3,4]pyrrolo-[1,2-a]indole-4,7-dione carbamate A solution of mitomycin A (76.6 mg. 0.22 mmol) in 3 ml of anydrous methanol was stirred at room temperature with p-aminomethylbenzenesulfonamide (80 mg). The mixture was kept at room temperature for 4 hours and at 0° C. for 12 hours. Solvent was removed by evaporation under reduced pressure. The dark residue was chromatographed using silica-gel as adsorbent. The fraction obtained by eluting the column with ethyl acetate was evaporated under reduced pressure to give 104 mg of the crude product. The crude product was dissolved in a minimum volume of methanol and anhydrous ether was added to this solution. The dark-blue precipitate was filtered and dried to give 52 mg (47% yield) of the desired product having a melting point of 93°–96° C. after crystallization from benzene and providing the following analysis:

NMR (DMSO-d$_6$,TMS): 'δ' in ppm. Absence of the 6-methoxy peak at 4.02 ppm and the appearance of new signals at 3.66–4.00 (broad s,2), 6.47(s,1) and 7.27–8.00(2d,6) were indicated.

With specific reference to the compounds comprehended by formula Ia, the above examples illustrate the following structural variations:

1. In the compounds of Examples 3, 4, 7, 13, 15 and 18, Y is lower alkyl and, more specifically, methyl. In all other examples, Y is hydrogen. The identity of Y is independent of the identity of Z (compare e.g., Examples 2 and 3 wherein Y is hydrogen and lower alkyl respectively, although Z has the same identity).

2. In Example 1, Z is thiazolamino; in Examples 2 and 3, Z is furfurylamino; in Example 4, Z is cyclopropylamino; and, in Example 5, Z is pyridylamino.

3. In Examples 6 through 25, Z is a radical of the formula

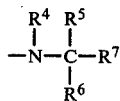

wherein $R^4$, $R^5$, $R^6$ and $R^7$ are set out above.

4. $R^4$, $R^5$ and $R^6$ may be the same or different and selected from among hydrogen and lower alkyl and may be selected independently of $R^7$. In some exemplary compounds (e.g., those of Examples 2 and 6), $R^4$, $R^5$ and $R^6$ are the same and are hydrogen, while in others (e.g., Example 10) $R^4$ is lower alkyl, and preferably methyl, while $R^5$ and $R^6$ are hydrogen. In still others (e.g., Example 11) $R^5$ and $R^6$ are the same and lower alkyl while $R^4$ is hydrogen.

The identity of the $R^7$ substituent is subject to wide variation, i.e., $R^7$ may be lower alkenyl (Examples 6, 7 and 8); halo-lower alkenyl (Example 9); lower alkynyl (Examples 10, 11, 12 and 13); lower alkoxycarbonyl (Example 14); halo-lower alkyl (Examples 15, 16 and 17); hydroxy-lower alkyl (Examples 18 and 19); pyridyl (Example 20); thienyl (Example 21); formamyl (Example 22); tetrahydrofuryl (Example 23); benzyl (Example 24); and benzene sulfonamide (Example 25).

6. Where $R^7$ is halo-lower alkyl or hydroxy lower alkyl, it is preferred that the halo or hydroxy group be attached to the terminal carbon atom of the alkyl group (i.e., the carbon atom distal to the atom attached to the ring). When $R^7$ is halo-lower alkenyl, it is preferred that the halo group be attached to a carbon atom other than the terminal carbon atom of the alkenyl radical. Finally, when $R^7$ is either alkenyl or alkynyl, it is preferred that the site of unsaturation in the carbon chain be at the terminal two carbon atoms of the radical.

Compounds according to the invention display antibacterial activity against gram-positive or gram-negative microorganisms in a manner similar to that observed for the naturally occurring mitomycins and are thus potentially useful as therapeutic agents in treating bacterial infections in humans and animals. Table I below provides data illustrative of such activity in the form of results of an antibacterial screening procedure involving mitomycin C and the compounds prepared according to Examples 4, 6, 12, 13 and 15. In the screening procedure, *Bacillus subtilis* was grown in a standard growth culture (pH6) and the test compound was placed on a 10 mm disk in the center of the culture plate. The measure of antibiotic activity was observation of the diameter of the zone surrounding the disk in which specified concentrations of test compound inhibited bacterial growth.

TABLE I

| | Zone of Inhibition (mm) vs. *B Subtilis* | | | | |
|---|---|---|---|---|---|
| | Concentration (mg/ml) | | | | |
| Compound | 12.5 | 3.1 | 0.8 | 0.2 | 0.005 |
| Mitomycin C | —(a) | — | 28 | 20 | 11 |
| Example 4 | — | 23 | — | — | — |
| Example 6 | 14.3 | 10.2 | 0(b) | 0 | 0 |
| Example 12 | — | 38 | 32 | 25 | 17 |
| Example 13 | 38 | 32 | 26 | 20 | 13 |
| Example 15 | 42 | — | — | 33 | 25 |

(a)indicates not tested.
(b)indicates no inhibitory activity observed.

Usefulness of compounds of formula Ia in the antineoplastic therapeutic methods of the invention is demonstrated by the results of in vivo screening procedures wherein the compounds are administered in varying dosage amounts to mice in which a P338 leukemic condition is induced. The procedures were carried out according to "Lymphocytic Leukemia P338—Protocol 1.200", published in *Cancer Chemotherapy Reports,* Part 3, Vol. 3, No. 2, page 9 (September, 1972). Briefly put, the screening procedures involved administration of the test compound to CDF$^1$ female mice previously infected with 10$^6$ ascites cells implanted intraperitoneally. Test compounds were administered on the first day of testing only, and the animals were monitored for vitality, inter alia, over a 35 day period.

Results of screening of compounds of Examples 1 through 25 are set forth in Table II below. Data given includes optimal dose ("O.D."), i.e., that dosage in mg/kg of body weight of the animal at which the maximum therapeutic effects are consistently observed. Also included is the median survival time ("MST") expressed as the MST of the test animals compared to the MST of controls×100 ("% T/C"). Within the context of the in vivo P388 procedure noted above, a % T/C value of 125 or greater indicates significant antineoplastic therapeutic activity. The lowest dose in mg/kg of body weight at which the 125% T/C value is obtained is known as the minimum effective dose ("MED"). These doses also are listed in Table II. It is worthy of note that the exceptionally high MST values obtained in the P388 screenings reported in Table II are also indicative of the absence of substantial toxicity of the compounds at the dosages indicated.

TABLE II

| EXAMPLE # | O.D. | MST as % T/C | MED |
|---|---|---|---|
| 1 | 1.6 | 167 | 0.2 |
| 2 | 12.8 | 276 | 0.4 |
| 3 | 12.8 | 256 | 1.6 |
| 4 | 12.8 | 167 | 6.4 |
| 5 | 3.2 | 211 | 0.2 |
| 6 | 6.4 | 150 | 3.2 |
| 7 | 6.4 | 189 | 3.2 |
| 8 | 25.6 | 245 | 1.6 |
| 9 | 25.6 | 178 | 3.2 |
| 10 | 6.4 | 210 | 0.8 |
| 11 | 25.6 | 178 | 1.6 |
| 12 | 12.8 | 358 | 0.2 |
| 13 | 25.6 | 300 | 1.6 |
| 14 | 12.8 | 300 | 0.4 |
| 15 | 51.2 | 205 | 6.4 |
| 16 | 12.8 | 190 | 1.6 |
| 17 | 12.8 | 140 | 12.8 |
| 18 | 12.8 | 272 | 1.6 |
| 19 | 25.6 | 244 | 3.2 |
| 20 | 12.8 | 167 | 3.2 |
| 21 | 12.8 | 167 | 3.2 |
| 22 | 3.2 | 217 | 0.4 |
| 23 | 12.8 | 289 | 0.4 |
| 24 | 25.6 | 194 | 1.6 |
| 25 | 25.6 | 150 | 6.4 |

Clearly among the most preferred compounds employed as antineoplastic agents according to the invention are those exhibiting more than twice the relative life-extending capacity generally characterized as evidencing significant therapeutic potential, i.e., those having an MST % T/C value greater than $2 \times 125$. The class of such compounds is seen to include the compounds of Examples 2, 3, 12, 13, 14, 18 and 23.

As may be noted from Table II, initial single dosages of as little as 0.2 mg/kg showed substantial long term antineoplastic activity. Accordingly, the methods of the invention may involve therapeutic administration of unit dosages of as little as 0.001 mg or as much as 5 mg, preferably from 0.004 mg to 1.0 mg, of the compounds as the active ingredient in a suitable pharmaceutical preparation. Such preparations may be administered in a daily regimen calling for from 0.1 mg to 100 mg per kg, preferably from about 0.2 to about 51.2 mg per kg, of the body weight of the animal suffering from neoplastic disease. It is preferred that the compounds be administered parenterally. Pharmaceutical compositions suitable for use in practice of methods of the invention may comprise simple water solutions of one or more of the compounds of formula Ia, but may also include well known pharmaceutically acceptable diluents adjuvants and/or carriers such as saline suitable for medicinal use.

Further aspects and advantages of the present invention are expected to occur to those skilled in the art upon consideration of the foregoing description and consequently only such limitations as appear in the appended claims should be placed thereon.

What is claimed is:

1. A method for treatment of a neoplastic disease state in an animal wherein the compounds administered are compounds of the formula,

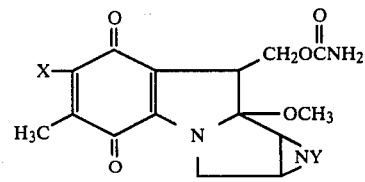

wherein: Y is hydrogen or lower alkyl; and X is a thiazolamino radical, a furfurylamino radical or a radical of the formula,

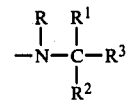

in which R, $R^1$, and $R^2$ are the same or different and selected from the group consisting of hydrogen and lower alkyl, and $R^3$ is selected from the group consisting of lower alkenyl, halo-lower alkenyl, lower alkynyl, lower alkoxycarbonyl, thienyl, formamyl, tetrahydrofuryl and benzene sulfonamide.

2. The method of claim 1 wherein the compound is selected from the group consisting of:

1,1a,2,8,8a,8b-hexahydro-8-(hydroxymethyl)-8a-methoxy-5-methyl-6(2-thiazol-amino) azirino[2',3':3,4]pyrrolo-[1,2-a]indole-4,7-dione carbamate;

1,1a,2,8,8a,8b-hexahydro-8-(hydroxymethyl)-8a-methoxy-5-methyl-6-furfurylamino-azirino[2',3':3,4-]pyrrolo-[1,2-a]indole-4,7-dione carbamate;

1,1a,2,8,8a,8b-hexahydro-8-(hydroxymethyl)-8a-methoxy-1,5-dimethyl-6-furfuryl-amino-azirino[2',3':3,4]pyrrolo-[1,2-a]indole-4,7-dione carbamate;

1,1a,2,8,8a,8b-hexahydro-8-(hydroxymethyl)-8a-methoxy-5-methyl-6-allylamino-azirino[2',3':3,4]pyrrolo-[1,2-a]indole-4,7-dione carbamate;

1,1a,2,8,8a,8b-hexahydro-8-(hydroxymethyl)-8a-methoxy-1,5-dimethyl-6-allylamino-azirino[2',3':3,4-]pyrrolo-[1,2-a]indole-4,7-dione carbamate;

1,1a,2,8,8a,8b-hexahydro-8-(hydroxymethyl)-8a-methoxy-5-methyl-6-(2-methylallyl-amino)-azirino[2',3':3,4]pyrrolo-[1,2-a]indole-4,7-dione carbamate;

1,1a,2,8,8a,8b-hexahydro-8-(hydroxymethyl)-8a-methoxy-1,5-dimethyl-6-(2-chloro-allylamino)-azirino[2',3':3,4]pyrrolo-[1,2-a]indole-4,7-dione carbamate;

1,1a,2,8,8a,8b-hexahydro-8-(hydroxymethyl)-8a-methoxy-5-methyl-6-(N-methyl-propargylamino)-azirino[2',3':3,4]pyrrolo-[1,2-a]indole-4,7-dione carbamate;

1,1a,2,8,8a,8b-hexahydro-8-(hydroxymethyl)-8a-methoxy-5-methyl-6-(1,1-dimethyl-propargylamino)-azirino[2',3':3,4]pyrrolo-[1,2-a]indole-4,7-dione carbamate;

1,1a,2,8,8a,8b-hexahydro-8-(hydroxymethyl)-8a-methoxy-5-methyl-6-proparylamino-azirino[2',3':3,4-]pyrrolo-[1,2-a]indole-4,7-dione carbamate;

1,1a,2,8,8a,8b-hexahydro-8-(hydroxymethyl)-8a-methoxy-1,5-dimethyl-6-propargyl-amino azirino[2',3':3,4]pyrrolo-[1,2-a]indole-4,7-dione carbamate;

1,1a,2,8,8a,8b-hexahydro-8-(hydroxymethyl)-8a-methoxy-5-methyl-6-(methoxycarbonyl-methylamino)-azirino[2',3':3,4]pyrrolo-[1,2-a]indole-4,7-dione carbamate;

1,1a,2,8,8a,8b-hexahydro-8-(hydroxymethyl)-8a-methoxy-5-methyl-6-(2-thienylmethyl-amino)-azirino[2',3':3,4]pyrrolo-[1,2-a]indole-4,7-dione carbamate;

1,1a,2,8,8a,8b-hexahydro-8-(hydroxymethyl)-8a-methoxy-5-methyl-6-(amenocar-bonylmethylamino)-azirino[2',3':3,4]pyrrolo-[1,2-a]indole-4,7-dione carbamate;

1,1a,2,8,8a,8b-hexahydro-8-(hydroxymethyl)-8a-methoxy-5-methyl-6-(2-tetrahydro-furfurylamino)-azirino[2',3':3,4]pyrrolo-[1,2-a]indole-4,7-dione carbamate;

1,1a,2,8,8a,8b-hexahydro-8-(hydroxymethyl)-8a-methoxy-5-methyl-6-[(4-sulphon-amidophenyl)methylamino]azirino[2',3':3,4]pyrrolo-[1,2-a]indole-4,7-dione carbamate.

3. The method of claim 1 wherein the amount of the compound administered comprises a daily dose of from about 0.2 mg. to about 51.2 mg. per kg. of the body weight of the animal.

4. A pharmaceutical composition for use in treatment of a neoplastic disease in an animal, said composition comprising a pharmaceutically acceptable solvent, diluent, adjuvant or carrier and, as the active ingredient, from about 0.001 to 5 mg. of a compound of the formula

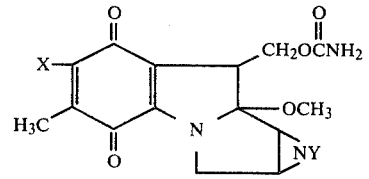

wherein: Y is hydrogen or lower alkyl; and X is a thiazolamino radical, a furfurylamino radical or a radical of the formula,

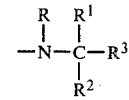

in which R, $R^1$, and $R^2$ are the same or different and selected from the group consisting of hydrogen and lower alkyl, and $R^3$ is selected from the group consisting of lower alkenyl, halo-lower alkenyl, lower alkynyl, lower alkoxycarbonyl, thienyl, formamyl, tetrahydrofuryl, and benzene sulfonamide.

* * * * *

UNITED STATES PATENT AND TRADEMARK OFFICE
CERTIFICATE OF CORRECTION

PATENT NO. : 4,460,599

DATED : July 17, 1984

INVENTOR(S) : William A. Remers

It is certified that error appears in the above-identified patent and that said Letters Patent is hereby corrected as shown below:

Abstract, Col. 2, line 5, "akloxycarbonyl" should be

-- "alkoxycarbonyl" --

Col. 2, line 12, "ment", should be -- "ments", --

Col. 2, line 66, "akloxycarbonyl" should be

-- "alkoxycarbonyl" --

Col. 3, line 38, "ispropyl" should be -- "isopropyl" --

Col. 4, line 63, "here" should be -- "hexane" --

Col. 5, lines 6 and 30, "[1,2a]" should be -- "[1,2-a]" --

Col. 6, line 3, "7.27 (s.2)," should be -- "7.27 (s,2)," --

Col. 6, line 42, "colum" should be -- "column" --

Col. 7, line 52, "CDl$_3$" should be -- "CDCl$_3$" --

Col. 7, line 58, "hydroxymethy)" should be

-- "hydroxymethyl)" --

Col. 9, line 7, "95°-97°" should be -- "95°-97°C" --

UNITED STATES PATENT AND TRADEMARK OFFICE
CERTIFICATE OF CORRECTION

PATENT NO. : 4,460,599

DATED : July 17, 1984

INVENTOR(S) : William A. Remers

It is certified that error appears in the above-indentified patent and that said Letters Patent is hereby corrected as shown below:

Col. 10, line 54, "pea_d_" should be -- "peak" --

Col. 10, line 55, "3,43-4.00" should be -- "3.43-4.00" --

Col. 11, line 12, "(decomposing and" should be

-- "(decomposing) and" --

Col. 11, line 36, "116°-11_8°_" should be -- "116°-118°C" --

Col. 12, line 57, "an_y_drous" should be -- "anhydrous" --

UNITED STATES PATENT AND TRADEMARK OFFICE
CERTIFICATE OF CORRECTION

PATENT NO. : 4,460,599
DATED : July 17, 1984
INVENTOR(S) : William A. Remers

It is certified that error appears in the above-indentified patent and that said Letters Patent is hereby corrected as shown below:

Col. 13, line 12, "anydrous" should be -- "anhydrous" --

Col. 16, line 63, "proparylamino" should be

-- "propargylamino" --

Col. 17, line 10, "amenocar-bonylmethylamino)" should be

-- "aminocarbonylmethylamino)" --

Signed and Sealed this

Twenty-fourth Day of August, 1993

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 4,460,599
DATED : July 17, 1984
INVENTOR(S) : William A. Remers

It is certified that error appears in the above-indentified patent and that said Letters Patent is hereby corrected as shown below:

Column 4, line 64, "colored" should be -- "purple-colored" --

Column 12, line 58, "2 ml" should be -- "1 ml" --

Signed and Sealed this

Nineteenth Day of April, 1994

Attest:

BRUCE LEHMAN

*Attesting Officer*   *Commissioner of Patents and Trademarks*